United States Patent [19]

Mudd et al.

[11] Patent Number: 5,217,690
[45] Date of Patent: Jun. 8, 1993

[54] ALL TANTALLUM STOPPED FLOW MICROCALORIMETER

[75] Inventors: Courtney Mudd, Great Falls, Va.; Robert Berger, Bethesda, Md.

[73] Assignee: The United States of America as represented by the Department of Health and Human Services, Washington, D.C.

[21] Appl. No.: 793,215

[22] Filed: Nov. 6, 1991

Related U.S. Application Data

[63] Continuation of Ser. No. 347,700, May 5, 1989, abandoned.

[51] Int. Cl.⁵ .......................................... G01N 25/48
[52] U.S. Cl. ............................. 422/51; 422/82.12; 436/147; 374/12
[58] Field of Search ............ 422/51, 82.12; 436/147; 374/10-12, 30

[56] References Cited

U.S. PATENT DOCUMENTS

| | | | |
|---|---|---|---|
| 3,303,689 | 2/1967 | Paulik et al. | 374/12 |
| 3,339,398 | 9/1967 | Barrall, II et al. | 374/11 |
| 3,491,581 | 1/1970 | Roberts et al. | 374/12 |
| 3,537,294 | 11/1970 | Stone | 374/13 |
| 3,552,207 | 1/1971 | Monk et al. | 374/30 X |
| 3,726,644 | 4/1973 | Desnoyers et al. | 422/51 X |
| 3,834,873 | 9/1974 | Picker | 436/145 |
| 3,856,467 | 12/1974 | Picker | 436/147 |
| 3,899,918 | 8/1975 | Privalov et al. | 374/11 |
| 3,972,681 | 8/1976 | Clack et al. | 422/51 X |
| 3,981,175 | 9/1976 | Hammond, III et al. | 374/10 |
| 3,981,487 | 9/1976 | Papoff et al. | 366/143 |
| 4,040,288 | 8/1977 | Kotelnikov et al. | 374/11 |
| 4,055,982 | 11/1977 | Ter-Minassian | 374/10 |
| 4,130,016 | 12/1978 | Walker | 422/51 X |
| 4,255,961 | 3/1981 | Biltonen et al. | 374/11 |
| 4,333,332 | 6/1982 | Privalov | 374/10 |
| 4,530,608 | 7/1985 | O'Neill | 374/11 |
| 4,783,174 | 11/1988 | Gmelin et al. | 374/33 |

OTHER PUBLICATIONS

Mudd et al., "An Optimized Differential Heat Conduction Solution Microcalorimeter for Thermal Kinetic Measurements", *Journal of Biochemical and Biophysical Methods*, vol. 6 (1982), pp. 179-203.

Primary Examiner—James C. Housel
Assistant Examiner—Jeffrey R. Snay
Attorney, Agent, or Firm—Low, Price, LeBlanc & Becker

10 Claims, 7 Drawing Sheets

ALL TANTALLUM STOPPED FLOW MICROCALORIMETER

This application is a continuation of application Ser. No. 07/347,700 filed May 5, 1989, now abandoned.

TECHNICAL FIELD OF THE INVENTION

This invention relates to apparatus for the determination of thermal properties of one or more fluid reactants and more particularly it relates to a computer controlled microcalorimeter which is capable of functioning in a stopped-flow manner.

BACKGROUND OF THE PRIOR ART

Thermal analysis encompasses an extremely wide spectrum of activities and a large variety of experimental methods and apparatus. The key thermal property measured is the heat capacity of a sample of known mass, from which the specific heat of the sample, which may be solid or liquid, can be calculated. Moreover, basic thermodynamic functions such as phase transition enthalpies as well as reaction kinetics can also be derived. In addition to measuring heat capacities, other heat effects which accompany chemical changes are also of great interest.

There are many approaches to measuring heats of reaction. These approaches include the classical calorimetric methods as well as various types of flow-through calorimeters methods. The prior art approaches to flow-through measurement of heats of reaction have, however, not been sufficiently stable nor sensitive to small changes in heats of reaction, particularly with regard to measurements involving small reactant concentrations. Moreover, the prior art approaches have been too sensitive to flow changes to permit precise measurements.

To date, most of the research involving calorimetric measurements has been carried out by means of known closed cell-type calorimeters. Flow calorimeters have been known and in use and their advantages over other types of calorimeters when dealing with fluid systems wherein chemical equilibrium is rapidly reached, are well recognized. Some highly sensitive forms of flow calorimeters have been developed and are generally referred to as flow microcalorimeters.

A significant improvement in the field of calorimeters has been the development of differential calorimeters. In general, a differential calorimeter is a sophisticated analytical instrument which measures thermal characteristics of a sample material. Specifically, in a differential calorimeter a sample channel and a reference channel are controllably heated over time and the temperature of each monitored. The thermal characteristics of the reference material are known and, preferably the reference material is chosen to be a material that does not undergo a transformation during analysis. Thus, when the sample material undergoes a transformation such as sublimation, boiling, reaction, or the like, that transformation is clearly discernable when compared to the reference material. By knowing the temperature at which a transformation occurs, as well as the energy either absorbed or expended during the transformation, the sample material can be rather accurately characterized.

Particularly in biological sciences, batch-type, heat-conduction microcalorimeters have been widely used. However, despite extensive refinements, motion artifacts and mixing problems together with reequilibration times between runs have limited the effective sensitivity to approximately 60 $\mu J$ and throughput to about 3 or 4 runs per day.

The present invention is a significant improvement over the prior art calorimetry methods and apparatus. In particular, the microcalorimeter of the present invention has a sensitivity that is three orders of magnitude greater than that for comparable microcalorimeters and is capable of attaining this sensitivity while using sample amounts which may be two orders of magnitude smaller than those used in other known microcalorimeters.

DISCLOSURE OF THE INVENTION

It is accordingly one object of the present invention to provide a highly sensitive microcalorimeter which is capable of achieving microjoule resolution.

Another object of the present invention is to provide a highly sensitive microcalorimeter which is computer-controlled.

A further object of the present invention is to provide a highly sensitive microcalorimeter which operates in a stopped-flow manner and utilizes a differential sensing system.

A still further object of the present invention is to provide a highly sensitive microcalorimeter having a unique structure which increases the effective differential sensitivity thereof.

A still further object of the present invention is to provide a computer-controlled stopped-flow microcalorimeter which is capable of achieving a high throughput.

An even further object of the present invention is to provide highly sensitive microcalorimetric methods for studying biological materials.

According to the present invention there is provided a computer-controlled all-tantalum stopped-flow microcalorimeter with microjoule resolution. The microcalorimeter of the present invention incorporates a unique mixer assembly and flow paths for reactants and reaction mixtures which increase the sensitivity for differential analysis.

Also provided by the present invention is a method of using the present microcalorimeter for measuring reaction heats of the order of 20-50 $\mu J$ at high throughput rates.

The present invention provides a method of measuring thermal properties of two or more fluids which comprises supplying said fluids to a differential microcalorimeter and periodically stopping the flow of fluids through the microcalorimeter while detecting thermal changes in the fluids.

With these and other objects in view, the present invention will be better understood from the description and the claims which follow hereinafter, taken with reference to the annexed drawings.

BRIEF DESCRIPTION OF DRAWING

The present invention will now be described with reference to the figures of the annexed drawings, which are given by way of non-limiting examples only in which.

DESCRIPTION OF THE PREFERRED EMBODIMENT

The stopped-flow differential microcalorimeter according to a preferred embodiment of the present invention comprises a mixer assembly, flow channels, and sensors which detect thermal changes occurring in each of the sample and reference flow channels. The mixer assembly for each channel as discussed below, is particularly designed to provide for rapid mixing of sample fluids so as to allow for higher throughput of samples. The flow channels, as discussed in more detail below, comprise means for supplying and removing fluid samples to the microcalorimeter. More particularly, the flow channels are designed and configured to increase the sensitivity of differential thermal detection by avoiding thermal changes of the fluids other than those changes caused by reactions between the fluids The sensors, which are positioned and arranged as described below, accurately detect and respond to thermal changes that occur in the sample fluids in the microcalorimeter.

Figure 1:
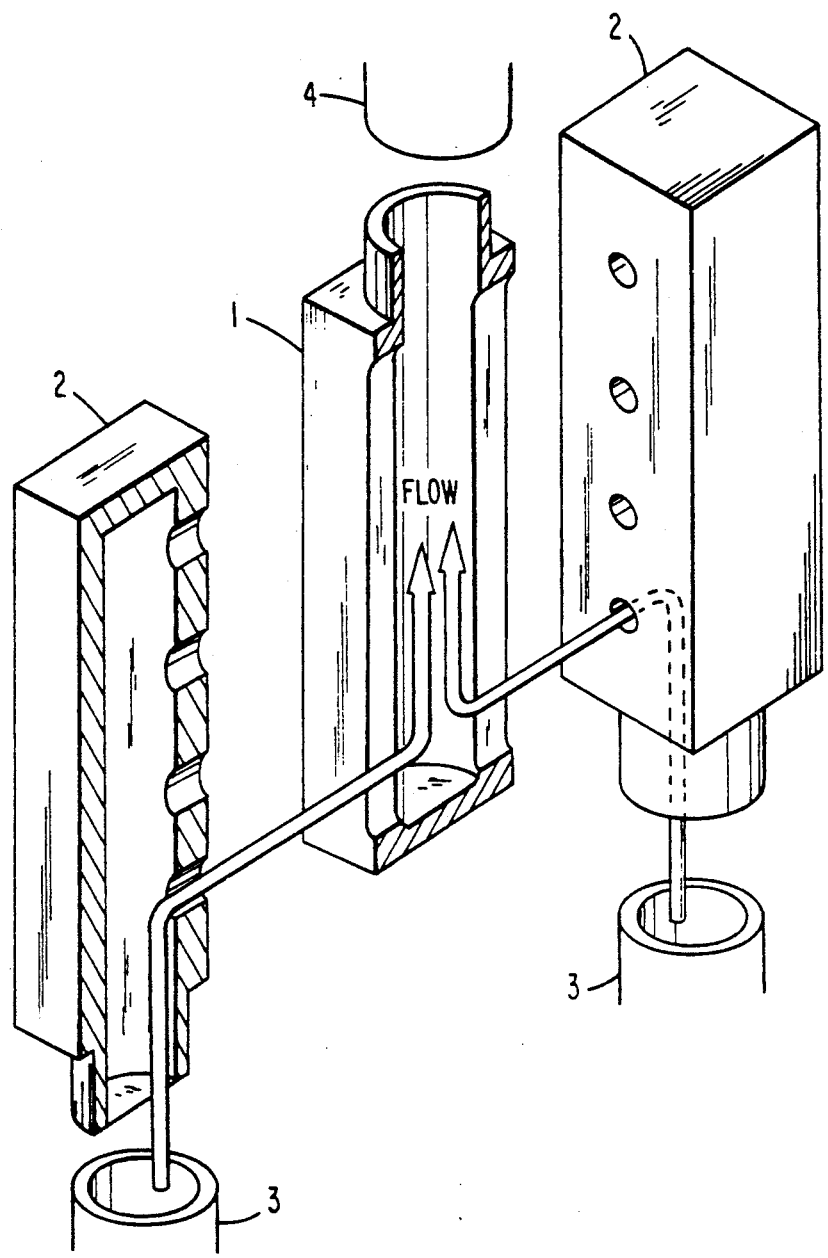
FIG. 1 is a diagram illustrating a preferred embodiment of an exemplary mixing assembly as used in conjunction with the present invention.
Figure 2D:
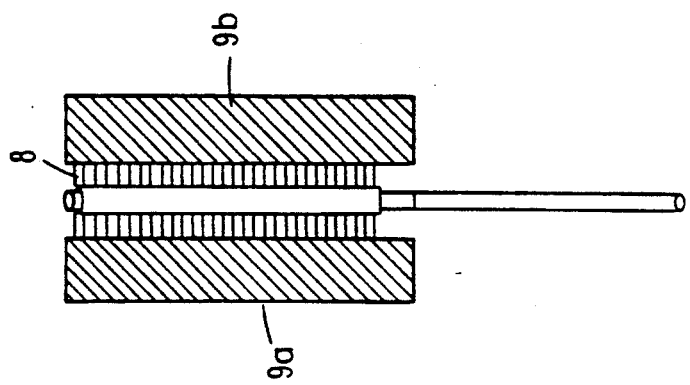
FIGS. 2(a)–(d) are diagrams illustrating the sensor and heater assemblies according to one embodiment of the differential microcalorimeter of the present invention.
Figure 2C:
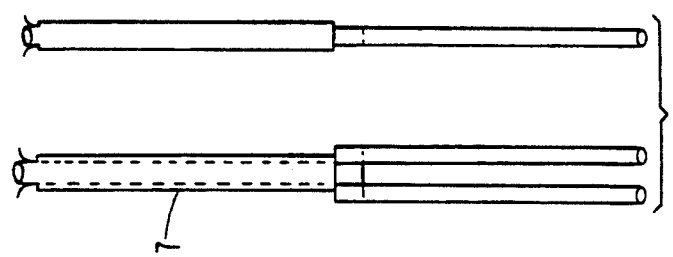
Figure 2B:
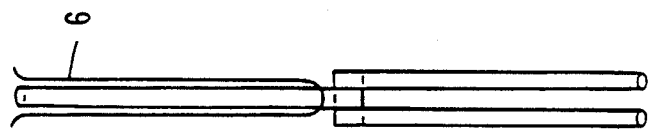
Figure 2A:
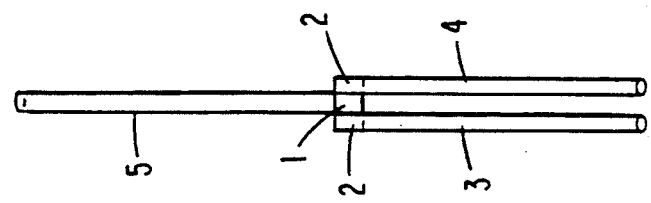

As illustrated in FIG. 1, the mixer assembly for each of the flow channels consists of three parts: a mixing chamber 1 and two entry ports 2 for each of the two entry lines 3. The entry and exit lines, 3 and 4 respectively are suitably sized tubing members which in a preferred embodiment preferably are tantalum tubing having an internal diameter of about 0.0625 inch and a wall thickness of about 0.009 inch. The mixer, ports, and tubing are preferably electron beam welded together.

FIGS. 2a-2d show the mixer assembly with attached tubing. Since the heat-sensing region of the exit tube 4 determines the reaction volume, it has been found necessary to limit this tube region to a suitable length, preferably 80 mm measured from the mixer assembly. It has been determined that a length which allows a maximum reaction volume of about 160 $\mu$l is preferred. As will be discussed below, substantially smaller reaction volumes have been found to be suitable without appreciable loss of sensitivity.

For electrical calibration and heating, a small insulated wire 6, about 0.1 mm diameter and about 300 mm long is wrapped around each exit tube 4 in the sensing region. See FIG. 2b.

I the preferred embodiment, a fluorocarbon insulated stainless steel wire is utilized for electrical calibration and heating purposes. Both the exit tube 4 and heater wire 6 are encased in a suitable thermally conductive material 7 such as Wood's metal to form a flat surface to interface with the sensors. See FIG. 2c. The heat detection scheme used in this instrument requires about 30 thermopiles for each flow channel The thermopiles 8 are equally divided, are placed on opposite sides of the exit tube 4, and are wired in series. The entire assembly is held in place by bolting together the two 9a, 9b of the sensor heat sink 9.

Figure 3:
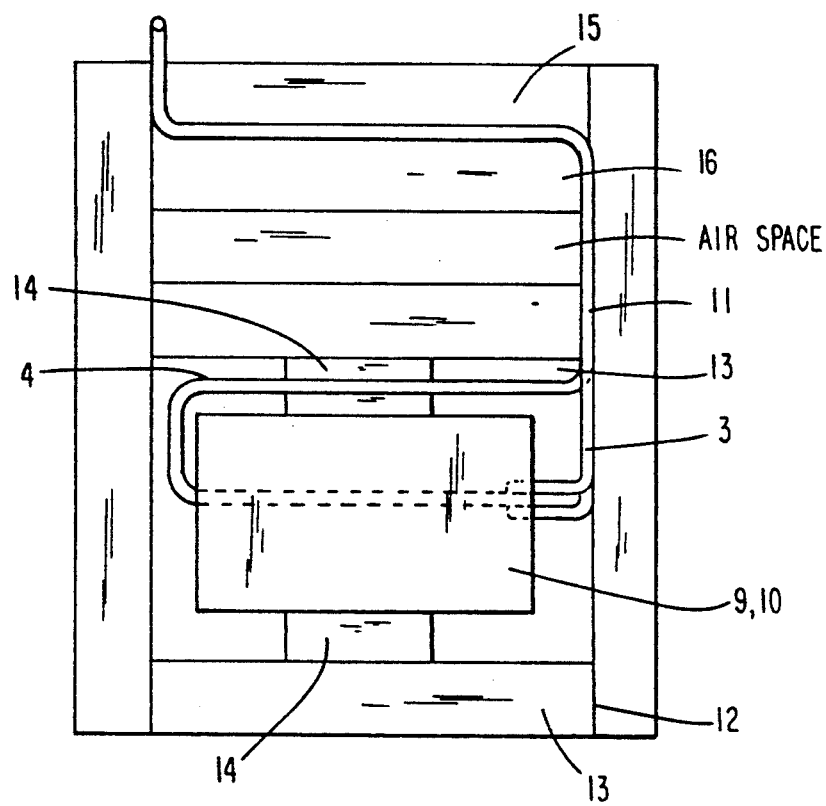
FIGS. 3 and 4 are diagrams illustrating a preferred arrangement of the inlet and exit tubes of the differential microcalorimeter according to the present invention.
Figure 4:
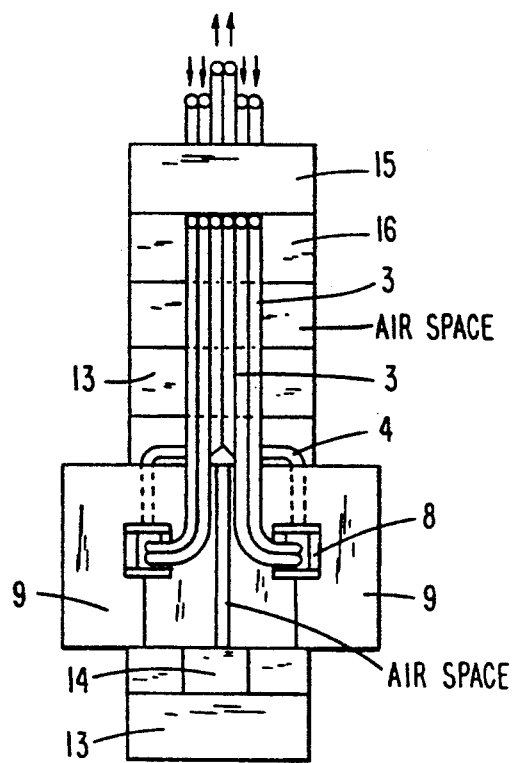
Figure 5:
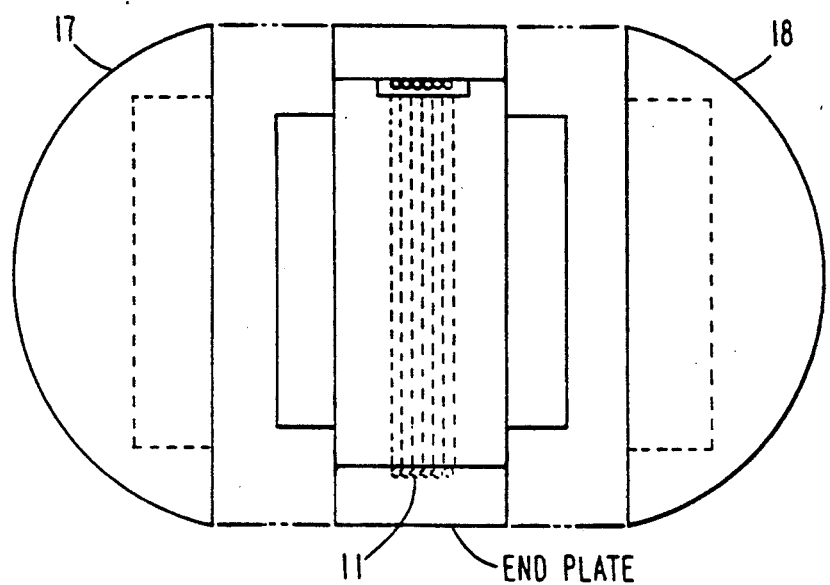
FIG. 5 is a diagram illustrating the complete core assembly according to one embodiment of the differential microcalorimeter of the present invention.

After exiting the sensor heat sink 9, the exit tubes 4 are routed around the sensor heat sink 9 to rejoin the inlet tubes 3 in a common groove 11 in the main heat sink as shown in FIGS. 3-5. At this point, all six tubes are located side by side and are potted in a suitable thermally conductive insulation material such as Wood's metal. This arrangement provides for a counter-current mode of heat exchange between the entering fluid and the exiting fluid to facilitate pre-equilibration before mixing. In addition, it also equilibrates all entering fluids to the same temperature so that any difference between the fluid temperature and the reference temperature of the sensor heat sinks for the sample and reference channels respectively will appear as a common-mode signal and thus be reduced by the common-mode rejection ratio of the instrument.

The electrical leads 10 from the respectively sensors and the calibration heaters are routed through a groove 12 in the bottom of the main heat sink 13. A four wire measurement scheme is used for each calibration heater The sensor heat sinks 9 for each channel are connected to the main heat sinks 13 through two small blocks 14. These small blocks 14 divide heat disturbances in the main heat sinks 13 equally between the sample and reference channels so that they are attenuated by the common-mode rejection ratio of the system. Such blocks are frequently termed "lenses" or "equipartition cones" as a result of their ability to direct the path of heat flow.

The six tubes leave the groove 11, then turn and run horizontally through two pre-equilibrator heat sinks 15 and 16 in the main heat sink before they turn and exit the core assembly. The groove is filled with a suitable conductor such as Wood's metal to improve pre-equilibration. Two caps 17 and 18 are attached to complete the core assembly as shown in FIG. 5. Cavities in the caps surround the sensor heat sinks 9. Thus, the only solid contact between the sensor heat sinks 9 and the main heat sinks 13 is through the blocks 14.

Figure 6:
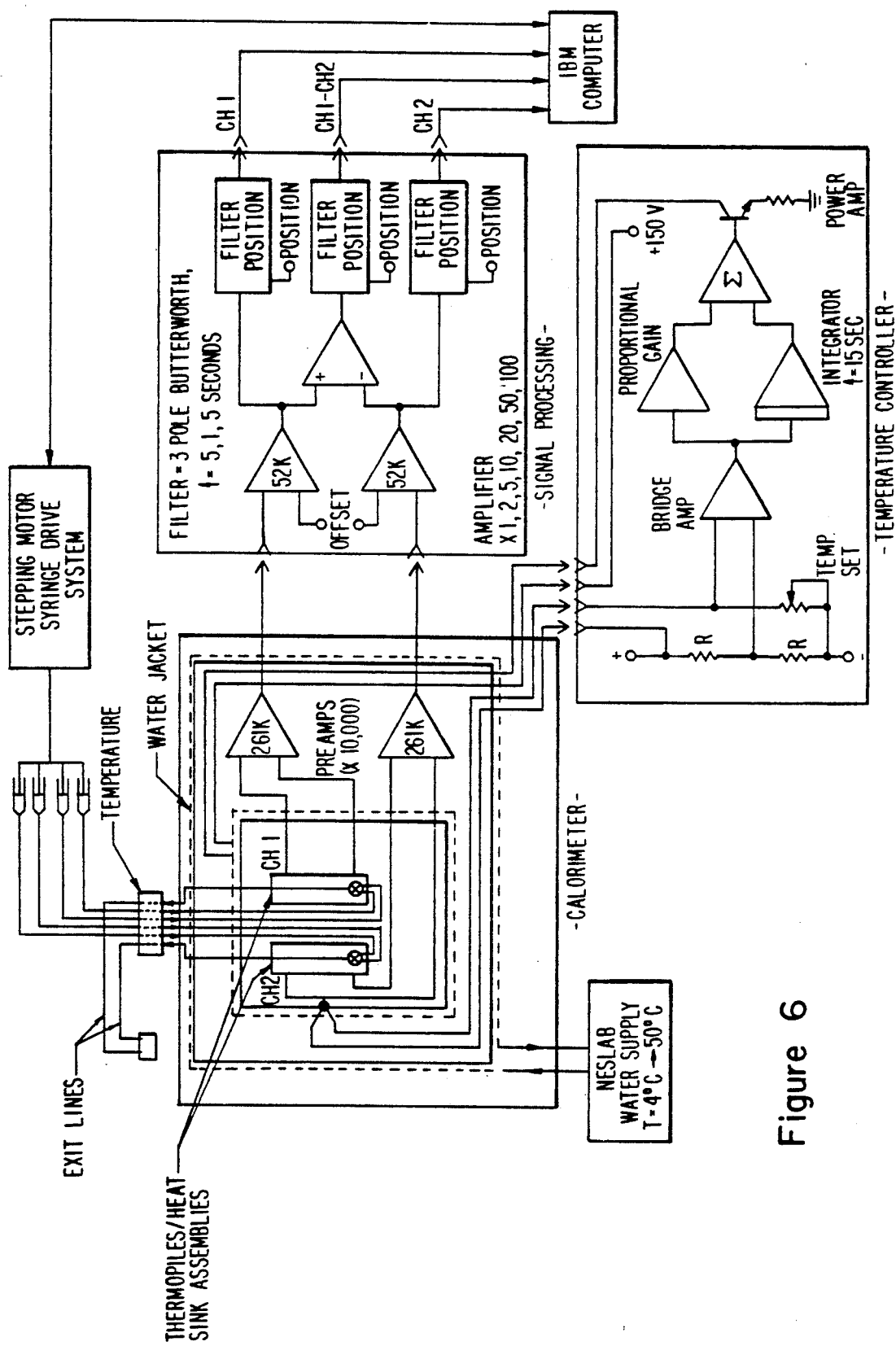
FIG. 6 is a schematic diagram illustrating the complete overall electrical circuitry of the differential microcalorimeter according to one the preferred embodiment of the present invention.

FIG. 6 shows an overall diagram of the complete instrument. The core/tubing assembly is mounted on thermally insulative, e.g., acrylic, standoffs inside a metal cylinder The cylinder is preferably made of aluminum, and in a preferred embodiment is about 8 inches in diameter, about 8 inches long and has a wall thickness of about 0.25 inch. Heaters are placed on the side, top, and bottom of cylinder. A thermistor for the core temperature controller is placed at a midpoint on the inside wall of the cylinder.

This temperature-controlled cylinder is placed in another insulative metal cylinder, on acrylic standoffs. This outer cylinder is preferably also made from aluminum and in a preferred embodiment is about 12 inches in diameter and about 15 inches long. The Preamplifiers are mounted on top of the inner cylinder and the space between the two cylinders is filled with a thermal insulation material such as polyurethane. The tubing is routed through openings in the top heater and through the top of the outer cylinder. The outer cylinder is positioned in a water jacket which may be made of plastic. A temperature-controlled water bath is used to pump water through the water jacket. This allows operation down to about 4° C. or up to about 50° C. The water supply temperature is usually kept about 5° C. below the set temperature of the core which allows the controller to heat the core above the "ambient temperature" maintained by the water jacket.

The entire assembly described above is, in turn, placed in an enclosure such as a plywood box and thermally insulated, preferably with polyurethane foam. The tubing exits through the top of the box and into a pre-equilibrator section which is controlled by solid-state heat pumps. The pre-equilibrator provides a constant temperature at the exit point of the tubing to prevent room temperature fluctuations from propagating down the tubing to the sensors and further provides some pre-equilibration for the fluids as they enter the calorimeter.

Figure 7:
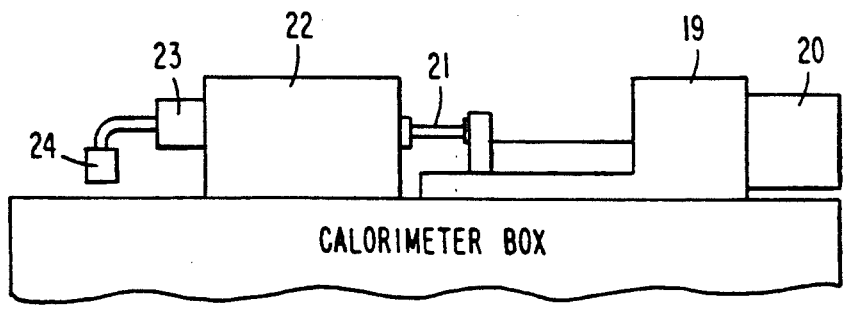
FIG. 7 is a schematic diagram illustrating the sample feed mechanism according to the preferred embodiment of the present invention.

A syringe drive assembly for generating the controlled fluid flows is shown in FIG. 7. The slide advance 19 is driven by a stepping motor 20. A preset indexer sets the number of steps for the motor and is controlled by a computer. The slide advance drives four syringes 21 which are mounted in a water jacketed holder 22 connected to the waterbath. Syringes of various sizes can be fitted to the holder. Preferred syringe sizes include 0.25 ml. 0.5 ml. 1.0 ml. and 2.5 ml syringes. This permits mixing of various ratios, such as 1:1, 1:2, 1:25, 1:4, 1:5 or 1:10 for the reacting fluids under study. The number of steps set into the preset indexer is adjusted with each chosen combination of reacting fluids to give the maximum reaction volume. The tubing and drive syringes are connected together with a 3-way valve 23 which allows loading through the third port. After leaving the valve, the tubing enters the pre-equilibrator 24.

Circuit block diagrams are shown in FIG. 6. The signal processing and temperature control consist of five separate functional elements (1) preamplifiers; (2) a bench amplifier; (3) a core controller; (4) a pre-equilibrator; and (5) data acquisition and run control.

The preamplifiers are chopper-stabilized d.c. amplifiers. The circuit is identical to one described by Mudd et al, "An Optimized Differential Heat Conduction Solution Microcalorimeter for Therma Kinetic Measurements", J. Biochem. Biophy. Methods 6, 179-203, incorporated herein by reference, except that with this instrument the closed loop gain is set at 10000. Low temperature coefficient resistors are used to minimize drift. To reduce electrical interference and keep temperature induced drift to a minimum, the preamplifiers are mounted in an R-F shielded box which is located between the inner and outer cylinders and which is preferably made of aluminum.

Figure 8A:
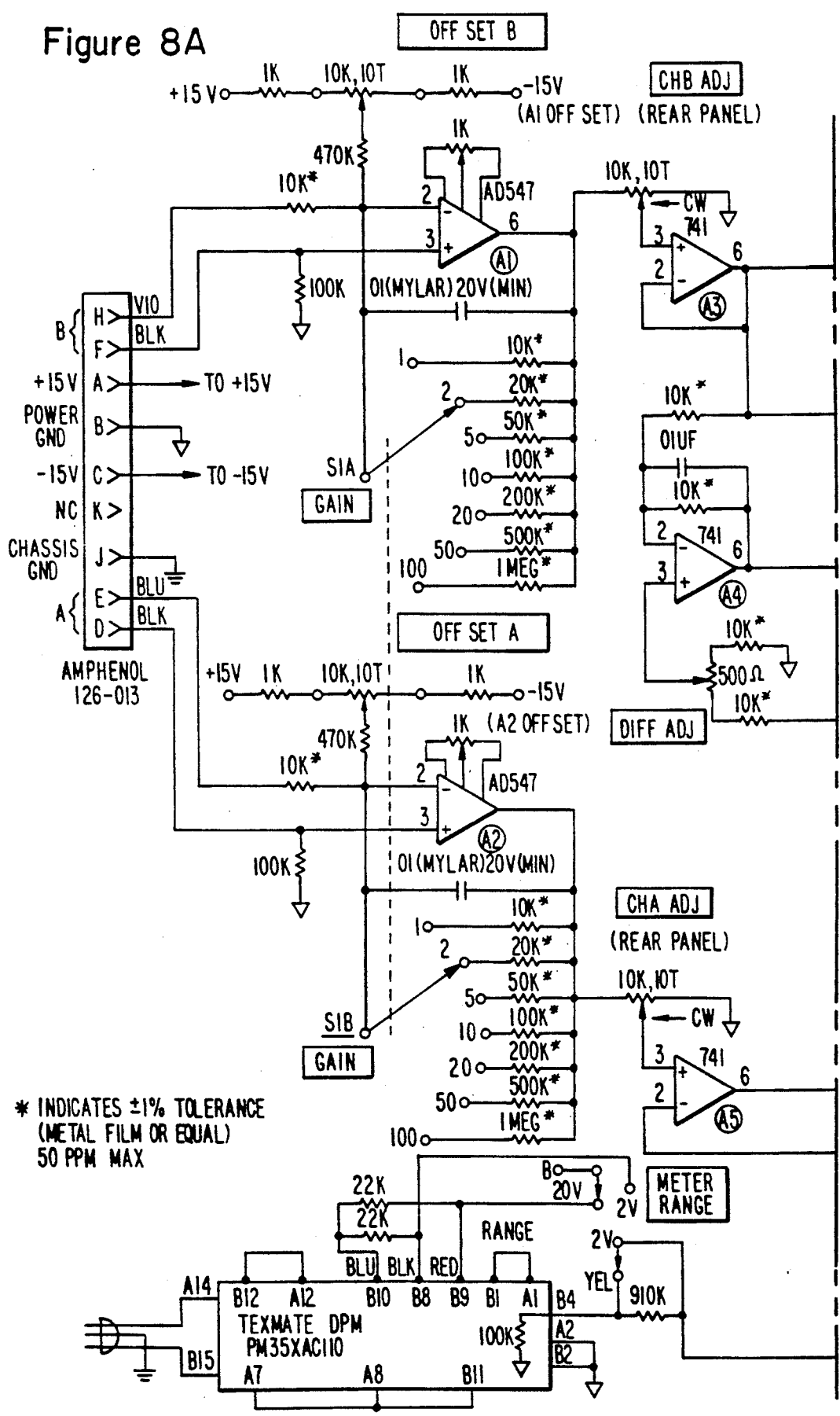
FIG. 8 is a schematic diagram of the amplifier circuit according to the preferred embodiment of the present invention.
Figure 8B:
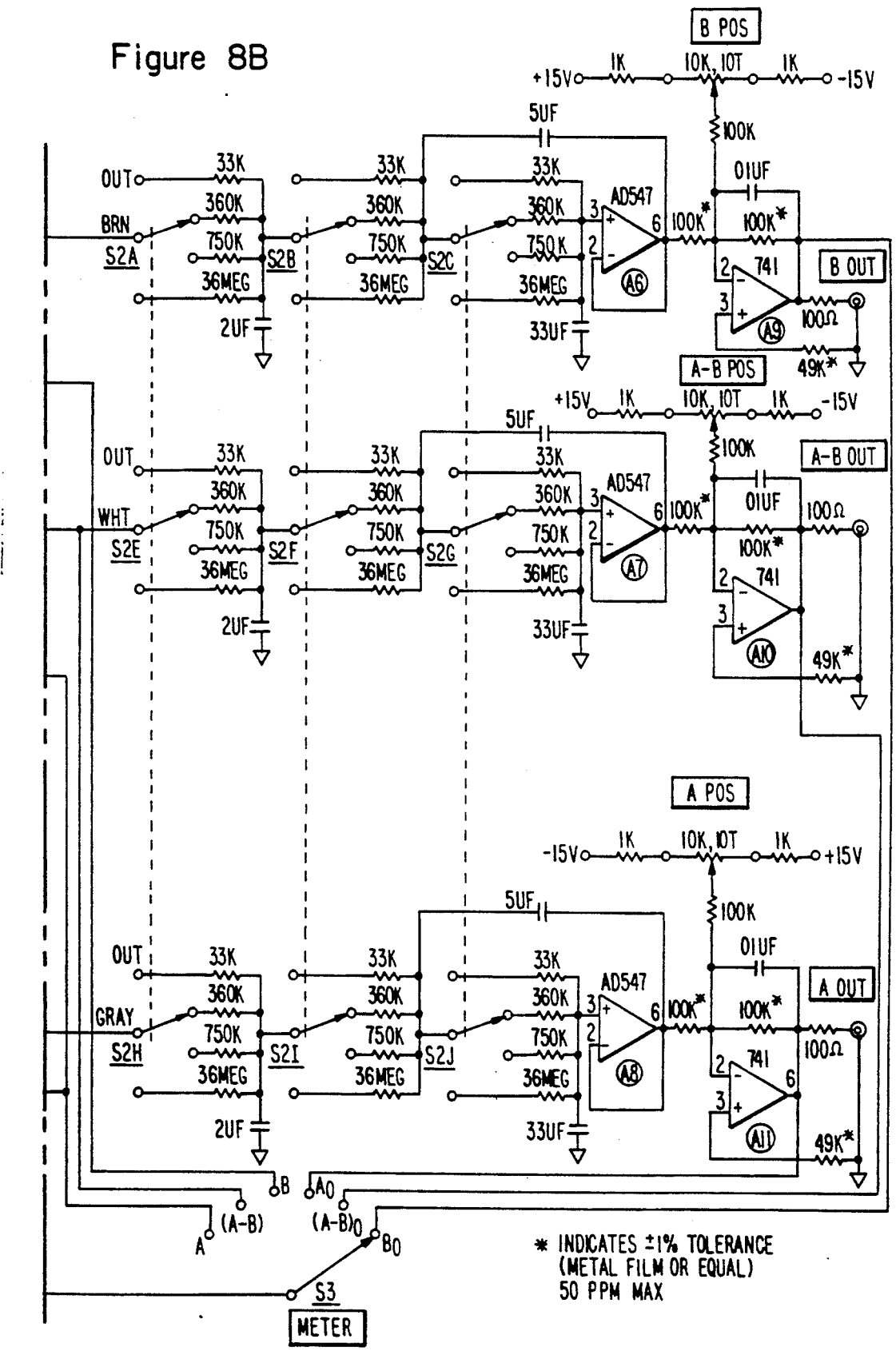

The bench amplifier unit FIG. 8 is located outside the calorimeter and performs the following functions: (1) additional, selectable gain: (2) gain balancing to match the channels; (3) subtraction to provide the differential output; and (4) selectable filtering. Amplifiers A1 and A2 provide the selectable gain and have provision for gain matching. Amplifiers A3 and A4 reduce the loading errors between the gain balance adjustments and the differential amplifier A5 which forms the differential output. The differential output is formed prior to filtering to insure that slight differences in the filter time constants will not degrade the dynamic common-mode rejection ratio of the electronics. Amplifiers A6, A7 and A8 form three separate 3-pole Butterworth filters which give maximally flat response in the bandpass region. The filter outputs are buffered by amplifiers A9, A10 and A11 which also allow output positioning or zeroing independent of the filter time constant The core temperature controller is a nulling type, proportional plus integral system and is identical to the one described by Mudd et al (J. Biochem. Biophy. Methods 6, 179-203 incorporated herein by reference.

The pre-equilibrator controller uses a linear feedback sensor which provides an output current linearly proportional to the absolute temperature of the sensor in Kelvin. With this circuit and a two point calibration, the total error over a 0°-50° C. operating range is less than 0.05° C. The output is fed directly to a digital panel meter which provides a readout of the pre-equilibrator temperature with a resolution of 0.1° C.

The set temperature for the pre-equilibrator is entered via a precision, linear, 10-turn potentiometer which has a digital dial to represent the temperature in a decimal format. The error voltage is fed to a proportional plus integral controller to minimize steady-state errors. A bipolar power supply is used so that the controller can automatically shift from heating to cooling. This allows the controller to regulate the temperature of the pre-equilibrator even when the set temperature is the same as the room temperature.

The final element in the signal processing system consists of the data acquisition and syringe drive control. For this instrument, a standard computer such as an IBM type computer (ZF-158-42; Zenith Data Systems Corp.) with a 16 bit analog to digital converter can be utilized. The computer acquires and stores all three outputs and controls the preset indexer which operates the syringe drive. The data acquisition program performs baseline corrections and integrates the data for total heat determinations in addition to screen plotting on the monitor. The data sample rate, run time, data storage, gain, and screen plot modes are user selectable.

In order to limit disturbances to the central core and minimize transient temperature gradients within the instrument, rapid loading and flushing into the core must be avoided. The following procedure exemplifies that used to run samples through the instrument.

The drive syringes are emptied through the loading ports and, if necessary, flushed several times before the sample is loaded. The valves are placed in the run position and the computer is used to inject 80 $\mu$l of each reagent every 150 s. The time of 150 s is used since it is the re-equilibration time of the reaction chamber. In this manner, the sensing portion of the instrument returns to thermal equilibrium before the next run. Since the priming volume (the volume from the loading port to the mixer) is 1 ml after 12 runs, the sample begins to reach the mixer and sample reactions appear. At this point an adjustment of the run time might be necessary. If the reaction is fast the instrument's time constant will appropriately limit the response to 150 s. If the reaction is slower than the instrument response however, the run time must be increased to allow the system to return to baseline and thus record all of the heat released by the reaction.

Since diffusion occurs at the sample interface, the first runs will usually be low. After about 4 runs, the reaction heats reach a steady-state value and represent valid runs. When the drive syringes have injected the entire sample and reached the end of their travel, they can either be reloaded with more reagents or a flushing solution depending upon the number of runs desired. 2.5 ml drive syringes may be used which, if reloaded with flushing solution after injecting the sample, will yield about 22-25 valid runs with a loss of 3-4 runs at each end of the sample bolus.

If the reaction is fast, each run will require 150 s. Thus, the total time required to load and run 2.5 ml of sample is about 110 min for approximately 22-25 valid runs. The overall time per run is then 4-5 min.

Thus, the present invention involves a microcalorimeter comprising at least one fluid inlet, at least one mixer assembly connected to each fluid inlet, at least one fluid outlet connected to each mixer assembly, at least one heater element surrounding at least a portion of each fluid outlet and a plurality of sensors surrounding at least a portion of each fluid outlet. Each of the mixing assemblies comprises a mixing chamber and at least one entry manifold connected to a fluid inlet and having a plurality of ports which connect to the mixing chamber.

In one preferred embodiment there are two entry ports for each one of the mixing assemblies and two mixing assemblies which include a pair of fluid inlets each.

In order to prevent back mixing between the mixing assembly and the inlet ports, it is important to keep the dimensions of the mixing assembly and the fluid inlets sufficiently small. In order to ensure thermal equilibrium within the microcalorimeter the mixing assemblies and the portion of the fluid outlets which are surrounded by the plurality of sensors are contained within at least two heat sink members with the fluid inlets and fluid outlets connected through opposite ends of the heat sink members. Additionally, these heat sink members are enclosed within a plurality of further heat sinks and the fluid inlets and the fluid outlets are located in a common, planar passage in the plurality of further heat sinks.

In a preferred embodiment all of the fluid inlets and outlets are made from tantalum.

In order to fully automate the microcalorimeter, fluid supply or sample supply means are connected to the fluid inlets. These fluid supply means comprise a plurality of pressure responsive fluid supply sources and means to apply a controlled pressure to said pressure responsive fluid supply sources. In a preferred embodiment, such pressure responsive fluid supply sources comprise syringes which may be actuated by means of a step motor.

In order to ensure accuracy the microcalorimeter includes means to calibrate and test the overall system. Such calibration is achieved by applying suitable electrical signals to the heating means.

A unique feature of the present microcalorimeter is the ability to measure thermal properties of two or more fluids in a stopped flow manner by periodically stopping the flow of fluids through the microcalorimeter while detecting thermal changes in the fluids. This manner of operation and the dimensions of the microcalorimeter allow the measuring of thermal properties of sample volumes of between about 25 $\mu l$ and about 160 $\mu l$.

A variety of different types of fluid samples can be investigated by the microcalorimeter of the present invention including fluids which chemically react together to produce a thermal change as well as biological samples.

EXAMPLES

The following examples were conducted to evaluate various features of the present invention. These examples are given for descriptive purposes only and the present invention is not intended to be considered as limited thereto. In the examples and throughout, signal voltage measurements are referred to the sensor leads (RTI, referred-to-input), i.e., the measured output voltages are divided by the overall gain.

EXAMPLE 1

In this example, a preliminary evaluation of the detection limits of the sensors was conducted utilizing the electrical heaters to thermally affect the system.

In order to determine the electrical base line noise, the input was shorted and detection was conducted at a filter time constant of 5 s. From this procedure it was determined that the system's electrical noise was approximately 60 nV at peak periods (p-p).

In order to test the systems response to abrupt thermal changes electrical pulse calibration tests were conducted. In these tests 3 heat bursts of 5 $\mu W$ (dQ/dT) having pulse widths of 2, 5 and 10 s were applied to the system utilizing the electrical heaters. From these tests it was discovered that a 2 s, 5 $\mu W$ heat burst was easily detectable (filter time constant=5 s).

Finally, in the preliminary evaluation of the system, measurements of the sensitivity constant of the system were conducted. In these tests an electrical step calibration input of 402 $\mu W$ produced an output change of 263 $\mu V$ indicating a sensitivity of 1.53 J/V.s or 1.53 W/V. Thus, the base line noise of 60 nV (p-p) discussed above was found to correspond to a thermal noise of 90 nW(p-p) with no flow. When the base line signal was integrated over 150 s for 25 runs and averaged, a value of 0.8±1.8 $\mu J$ was obtained. When the heat bursts were integrated, a calibration constant of 1.56J/V.s was obtained As with batch calorimeters, electrical sensitivity measurements tend to be overly optimistic since major sources of noise, e.g. mixing in flow artifacts, often degrade the effective usable sensitivity.

EXAMPLE 2

In this example 25 runs of 80 $\mu l$ water/water mixes each lasting 200 s were performed in order to evaluate the systems overall performance. Integrated heats of the water/water mixes were performed in both single and differential output modes Table 1 below shows the integrated heats for 5 of these runs. In this example it was discovered that there is a flow artifact in the single channel but, since it was also present in the other channel, the differential output remains low. The common-mode rejection ratio (CMRR) is defined as the ratio of the common-mode signal (CH1) to the differential output (CH1 - CH2). In this example, we have a measure of the AC common-mode rejection ratio since our signa is pulsatile and has no DC component. From Table 1, it is seen that the AC common-mode rejection ratio of the 5 flow artifacts is approximately 60.

This example shows the value of a differential scheme in reducing common-mode signals. With a differential system, there is no longer a need to control mixing heats, thermal dis-equilibriums etc., as long as both channels experience the same disturbance. In exchange, the ability to make absolute heat determinations is lost and, instead, the relative difference between the two channels is determined. For large signals where common-mode noise is not a problem, the instrument can be operated single-ended by recording from either of the two channels. In this mode of operation absolute heat measurements are possible.

By averaging 25 runs of a water/water mix the average value of 0.9±2.1 μJ represents a more realistic measurement of the instruments resolution than simple electrical tests since this value was obtained under actual flow conditions. This flow value is only slightly higher than the non-flow value obtained from the integration of the base line only.

TABLE 1

INTEGRATED HEATS OF WATER/WATER MIXES

| Run no. | Integrated heats (μJ) | |
|---|---|---|
| | CH1 | CH1—CH2 |
| 1 | 77.9 | −1.8 |
| 2 | 63.8 | −0.5 |
| 3 | 63.4 | −1.1 |
| 4 | 73.2 | +0.5 |
| 5 | 70.3 | −2.0 |

EXAMPLE 3

To evaluate the effect of the diffusion at the sample interface in the tube, the heat of dilution of 0.1 M NaCl to 0.05 M which releases approximately 430 μJ was used. All solutions used in these calibrations were made from Fisher reagent grade supplies. It was important that all water be distilled and degassed before use to prevent the formation of bubbles due to outgassing. 2.5 mL of 0.1 M NaCl was loaded into one drive syringe of channel 1 and distilled, deionized water was loaded into the other three drive syringes. The computer then ejected the sample into the calorimeter with 150s run times until the drive syringe was empty. At this point, the drive syringe was flushed several times through the loading port and then all the drive syringes were re-loaded with distilled, deionized water. Utilizing the resulting thermograms, and taking an average of 20–25 runs as valid heats and using 95% of this value as a cutoff, 25 valid runs were obtained out of possible 31. With a cutoff of 98% of the mean value, 22 valid runs were still obtained.

EXAMPLE 4

To evaluate the magnitude and any effect of back diffusion through the mixers similar runs to those of Example 3 were utilized in measuring the heat of dilution of 0.1 M NaCl to 0.05 M. The samples were loaded and run as in Example 3 until the middle of the sample bolus was reached at which time the run was stopped. After 12 hours, the runs were resumed. The results show that after 3 runs, the reaction heats were back to within 5% of the steady-state value. Since the Na and Cl ions are very small and highly mobile, this result shows that during a typical run of 200s, the back diffusion affect is negligible especially for large macromolecules frequently used in biological work.

EXAMPLE 5

With the mixing protocol established, a run of a series of chemical calibrations was conducted. The following heat of diluting reactions were used: 0.1 M sucrose to 0.05 M; 0.01 M NaCl to 0.005 M; 0.1 M NaCl to 0.05 M; 0.8 M NaCl to 0.4 M; 0.01 N HCl to 0.005 N; 0.1 N HCl to 0.05 N; 0.2 N HCl to 0.1 N and; 0.555 N HCl to 0.278 N. The results of this series of runs is summarized in Table 2 below.

TABLE 2

RESULTS OF CHEMICAL CALIBRATIONS

| | Reaction (1:1 dil) | Time (s) | Area (μV · s) | Enthalpy (μJ) | K. (J/V · s) |
|---|---|---|---|---|---|
| 1. | 0.1 M Sucrose | 200 | 138.2 ± 1.7 | 222.2 | 1.607 ± 0.020 |
| 2. | 0.01 M NaCl | 200 | 22.4 ± 2.1 | 36.6 ± 1.7 | 1634 ± 0.153 |
| 3. | 0.01 M NaCl | 200 | 22.4 ± 2.1 | 32.3 ± 0.3 | 1.442 ± 0.135 |
| 4. | 0.1 M NaCl | 300 | 268.5 ± 2.6 | 433 ± 17 | 1.613 ± 0.016 |
| 5. | 0.1 M NaCl | 300 | 268.5 ± 2.6 | 506 ± 5.1 | 1.885 ± 0.019 |
| 6. | 0.8 M NaCl | 300 | −9513 ± 11 | −16770 ± 335 | 1.763 ± 0.020 |
| 7. | 0.8 M NaCl | 300 | −9513 ± 11 | −15360 ± 307 | 1.615 ± 0.032 |
| 8. | 0.01 N HCl | 200 | 28.7 ± 2.4 | 43.5 ± 1.7 | 1.516 ± 0.127 |
| 9. | 0.1 N HCl | 300 | 759.0 ± 2.7 | 1206 ± 17 | 1.589 ± 0.024 |
| 10. | 0.2 N HCl | 300 | 2097 ± 9 | 3261 ± 33 | 1.555 ± 0.016 |
| 11. | 0.555 N HCl | 300 | 10030 ± 9 | 15330 ± 100 | 1.528 ± 0.010 |

[a]Larger standard deviations in K are due to the small values of heat of dilution at these low concentrations.
[b]Endothermic reactions.

A linear regression analysis of the data in Table 2 reveals a calibration constant with an intersect of 1.603 J/V.s and a slope of +2.2(J/V.s)/J. Thus, over a 15 mJ range, the system is linear within 2%. Slight differences in the sensitivity which were detected may not be real since there are conflicting values published in the literature. The difference between the chemical calibration constant of 1.6J/V.s and the electrical pulse constant of 1.56J/V.s is most likely due to the fact that the electrical heater is not in the sample solution and is slightly closer to the sensors.

EXAMPLE 6

In each of the preceding experiments, the full measure volume of 160 μl was used. In order to evaluate the effect of using a smaller portion of the measurement tube, a dilution of 0.1 N HCl to 0.05 N was used and the volume of the mixture was varied. The results are given in Table 3 below. From Table 3 it is seen that there is only a slight loss of sensitivity when utilizing smaller mixing volumes.

TABLE 3

SENSITIVITY OF CALIBRATION CONSTANT TO SAMPLE VOLUME

| Sample volume (μl) | Area (μV · s) | Enthalpy (μJ) | K (J/V · s) |
|---|---|---|---|
| 27 | 223 | 402 | 1.81 |
| 40 | 366 | 603 | 1.66 |
| 53 | 502 | 804 | 1.61 |
| 67 | 624 | 1005 | 1.61 |
| 80 | 759 | 1206 | 1.60 |
| 93 | 890 | 1407 | 1.59 |

EXAMPLE 7

In order to evaluate the temporal resolution possible with the present system, a thermogram of the 0.01 N HCl calibration in Example 3 above was decomposed utilizing an interactive data decomposition scheme and expanded. Likewise, a thermogram from two, 1 s, 50 $\mu$W electric calibration pulses spaced 1 s apart were similarly decomposed and expanded. There was no dimensional change in the measured output signals since the decomposition procedure is functionally a bandwidth enhancement scheme. The use of this data decomposition has the effect of creating a stopped-flow microcalorimeter with a 1 s rise-time.

The stopped-flow microcalorimeter of the present invention has been found to be capable of operating at 120 runs/8 hours routinely with a standard deviation of $\pm 3$ $\mu$J. With this system, up to 120 binding enthalpies/day in the 20–50 $\mu$J range with the standard deviation of $\pm 3$ $\mu$J have been easily obtained.

From the above examples it is seen that the stopped-flow microcalorimeter of the present invention is characterized as having superior sensitivity utilizing extremely small sample volumes.

Although the invention has been described with reference to pa particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims that follow.

We claim:

1. A differential microcalorimeter for rapid stopped-flow calorimetric analysis of very small amounts of reactive materials, comprising:
    a first channel formed to have a predetermined fluid flow and heat transfer characteristic, for controllably channeling a predetermined amount of a mixture of selected reactive materials therethrough;
    a second channel formed to have a fluid flow and heat transfer characteristic matching said predetermined characteristic of said first channel, provided in a predetermined heat exchange relationship with respect to said first channel, for controllably channeling a predetermined amount of a non-reactive reference mixture comprising at least one of said selected materials therethrough, wherein each of said first and second channels includes an inlet to each receive a predetermined amount of the respective material therethrough, and further wherein the first and second channels are formed of tantalum;
    at least one mixing assembly connected to each of the first and second channels to form a stopped mixture of said materials received therethrough,
    an outlet channel connected to each mixing assembly, the outlet channels being formed of tantalum and being in a counter-current mode of heat exchange with the first and second channels;
    a heater element surrounding at least a portion of each outlet channel;
    a plurality of sensors surrounding at least a portion of each outlet channel and each mixing assembly;
    a sensor heat sink surrounding the plurality of sensors, a main heat sink surrounding the sensor heat sink and the first, second and outlet channels at a location where the outlet channels are in the counter-current mode of heat exchange with the first and second channels, and at least one thermal lens connecting the sensor heat sink with the main heat sink; and
    means for controllably supplying a predetermined amount of the respective materials to the inlet of the first and second channels.

2. A microcalorimeter according to claim 1, wherein: the volume of each mixing assembly and the size of the first and second channels are made sufficiently small so as to prevent significant back mixing of materials from each mixing assembly.

3. A microcalorimeter according to claim 1, further comprising:
    means to calibrate said microcalorimeter.

4. A microcalorimeter according to claim 1, comprising two of said mixing assemblies, each of which is connected to the first and second channels, respectively, and has an outlet channel connected thereto, with each outlet channel being in a counter-current mode of heat exchange with the first and second channels.

5. A microcalorimeter according to claim 1, wherein:
    each mixing assembly comprises a mixing chamber and at least one entry manifold connected to each of the first and second channels, respectively,
    said at least one entry manifold having at least one port which communicates with said mixing chamber.

6. A microcalorimeter according to claim 5, wherein: said at least one port comprises two entry ports, each of which entry ports communicates with the mixing chamber.

7. A microcalorimeter according to claim 1, wherein: the sensor heat sink comprises two heat sink members and each of the first and second channels and the outlet channels connect to each respective mixing assembly through opposite ends of the two heat sink members.

8. A microcalorimeter according to claim 7, wherein: the first and second channels and the outlet channels are located substantially in a common plane in the main heat sink.

9. A microcalorimeter according to claim 1, wherein: the means for controllably supplying the respective materials to the inlets of the first and second channels comprises a plurality of pressure-responsive supply sources and means to apply a controlled pressure to each of said pressure responsive supply sources.

10. A microcalorimeter according to claim 9, wherein: said pressure responsive supply sources comprise respective coacting syringes to provide successive predetermined amounts of the respective materials.

* * * * *